United States Patent [19]

Taylor et al.

[11] Patent Number: 4,831,037

[45] Date of Patent: May 16, 1989

[54] 4(3H)-OXO-5,6,7,8-TETRAHYDROPYRIDO-(2,3-D)PYRIMIDINE DERIVATIVES

[75] Inventors: Edward C. Taylor, Princeton, N.J.; George P. Beardsley, Essex, Conn.; James M. Hamby, Plainsboro, N.J.

[73] Assignee: The Trustees of Princeton University, Princeton, N.J.

[21] Appl. No.: 40,330

[22] Filed: Apr. 20, 1987

[51] Int. Cl.$^4$ .................. A61K 31/505; C07D 471/04; C07F 7/08
[52] U.S. Cl. .................................... 514/258; 544/279; 544/229
[58] Field of Search ................. 514/258; 544/279, 229

[56] References Cited

U.S. PATENT DOCUMENTS 4,684,653 8/1987 Taylor et al. ...................... 544/279

OTHER PUBLICATIONS

Dedhar et al., *Biochemical Pharmacology* 32, pp. 922-924 (1983).
Dedhar et al., Chem. Abstract No. 16099u, vol. 99 (1983).
Taylor et al., *J. Org. Chem.* 48, p. 4852 (1983).
Temple et al., *J. Med. Chem.* 24, p. 1254 (1981).

Primary Examiner—Donald G. Daus
Assistant Examiner—E. Bernhardt
Attorney, Agent, or Firm—Bruce M. Collins

[57] ABSTRACT

N-[4-(N'-[2-amino-4(3H)-oxo-5,6,7,8-tetrahydropyrido[2,3-d]pyrimidin-6-ylmethyl]-N'-acylamino)-benzoyl]-L-glutamic acid derivatives are antineoplastic agents. The compounds are prepared through acylation of the corresponding N'-amino compound or hydrolysis of a protected N'-acylamino compound. A typical embodiment is N-[4-(N'-[2-amino-4(3H)-oxo-5,6,7,8-tetrahydropyrido[2,3-d]pyrimidin-6-ylmethyl]-N'-formylamino)benzoyl]-L-glutamic acid.

15 Claims, No Drawings

(3H)-OXO-5,6,7,8-TETRAHYDROPYRIDO-(2,3-D)PYRIMIDINE DERIVATIVES

DESCRIPTION

1. Technical Field

The invention pertains to N-[4-(N'-[2-amino-4(3H)-oxo-5,6,7,8-tetrahydropyrido[2,3-d]pyrimidin-6-yl-methyl]-N'-acylamino)benzoyl]-L-glutamic acid derivatives, which are antineoplastic agents, to salts thereof, to the preparation and use of the compounds and their salts, and to intermediates useful in those preparations.

2. Background Art

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from the dihydrofolate which is formed during the conversion of 2-deoxyuridylate to thymidylate by the enzyme thymidylate synthetase.

Other derivatives of folic acid and aminopterin have been synthesized and tested as antimetabolites. Among these are compounds in which a methylene or methylidene group occupies a position in the molecule normally occupied by an imino or nitrilo group, respectively. These derivatives have varying degrees of antimetabolic activity. 10-Deazaaminopterin is highly active (Sirotak et al., *Cancer Treat. Rep.*, 1978, 62, 1047) and 5-deazaaminopterin has activity similar to that of amethopterin (Taylor et al., *J. Org. Chem.*, 1983, 48, 4852). 8,10-Dideazaaminopterin is reported to be active (U.S. Pat. No. 4,460,591) and 5,8,10-trideazaaminopterin exhibits activity against mouse L1210 leukemia (Yan et al., *J. Heterocycl. Chem.*, 1979, 16, 541). 10-Deazafolic acid, on the other hand, shows no significant activity (Struck et al., *J. Med. Chem.*, 1971, 14, 693) and 5-deazafolic acid is only weakly cytotoxic. 8,10-Dideazafolic acid is only marginally effective as a dihydrofolate reductase inhibitor (De Graw et al., "Chemistry and Biology of Pteridines", Elsevier, 1979, 229) and 5,8,10-trideazafolic acid also shows only marginal activity against mouse L1210 leukemia (Oatis et al., *J. Med. Chem.*, 1977, 20, 1393). 5,10-Dideazaaminopterin and 5,10-dideaza-5,6,7,8-tetrahydroaminopterin, and the corresponding 5,10-dideazafolic acid derivatives are reported by Taylor et al., *J. Med. Chem.*, 28:7, 914 (1985).

DISCLOSURE OF INVENTION

The invention pertains to 4(3H)-oxo-5,6,7,8-tetrahydropyrido[2,3-d]pyrimidines of the formula:

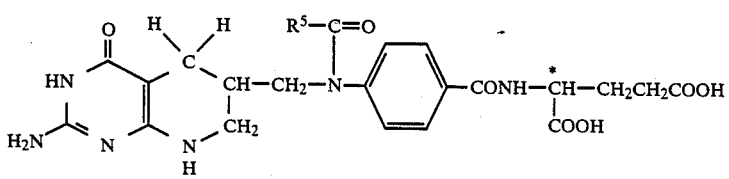

wherein $R^5$ is hydrogen or alkyl of 1 to 6 carbon atoms and the configuration about the carbon atom designated * is L; the tautomeric forms thereof; and the pharmaceutically acceptable salts thereof.

The invention also pertains to methods for the preparation of such compounds, to intermediates useful in those preparations, and to methods and compositions for the use of such compounds in combating neoplastic growth.

Modes For Carrying Out The Invention

The compounds of the invention are derivatives of the 5,6,7,8-tetrahydropyrido[2,3-d]pyrimidine heterocyclic ring which is numbered as follows:

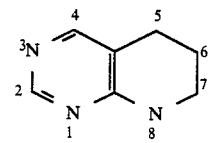

The compounds of Formula I exist in tautomeric equilibrium with the corresponding 4-hydroxy compound:

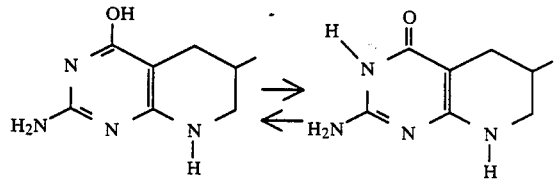

For convenience, the 4(3H)-oxo form is depicted, and the corresponding nomenclature is used, throughout this specification, it being understood that, in each case, such designations include the corresponding tautomeric 3,4-dehydro-4-hydroxy form.

The absolute configuration about the carbon atom designated * in the glutamic acid chain is L, being the same absolute configuration as that about the corresponding alpha carbon atom in alanine. The carbon atom in the 6-position of the 5,6,7,8-tetrahydropyrido[2,3-d]pyrimidine ring system also is a chiral center, leading to d,L- and l,L-diastereoisomers. Both forms, which can be separated mechanically as by chromatography, are within the scope of the invention.

The invention includes the pharmaceutically acceptable salts. Salts with either acid (involving the nitrogen atom in the 8-position) or base (involving the carboxylic acid groups in the glutamic acid residue) can be formed. Those formed from base include the alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like. Those formed from acid include pharmaceutically acceptable, non-toxic acid addition salts, such as are formed from (i) inorganic acids, as for example hydrochloric acid, hydrobromic acid, nitric acid, sulfuric acid, phosphoric acid, and the like (ii) organic carboxylic acids, as for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 4-phenoxybenzoic acid, 2-acetoxybenzoic acid, embonic acid, nicotinic acid or isonicotinic acid, and (iii) organic sulfonic acids, as for example methansulfonic acid, ethanesulfonic acid, 2-hydroxyethanesulfonic acid, ethane-1,2-disulfonic acid, benzenesulfonic acid, p-toluenesulfonic acid or naphthalene-2-sulfonic acid.

The compounds of this invention and their salts have an effect on one or more enzymes which utilize folic acid, and in particular metabolic derivatives of folic acid, as a substrate.

The compounds of Formula I can be prepared in a first process by selective hydrolysis of a 2-amino-4(3H)-oxo-5,6,7,8-tetrahydropyrido[2,3-d]pyrimidinyl-L-glutamic acid derivative of the formula:

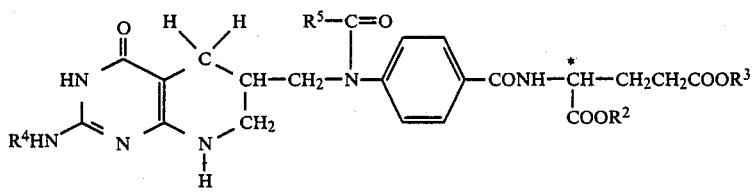

wherein
$R^2$ and $R^3$ are the same or different carboxylic acid protecting group;
$R^4$ is an amino protecting group;
$R^5$ is hydrogen or alkyl of 1 to 6 carbon atoms; and the configuration about the carbon atom designated * is L.

Protecting groups encompassed by $R^2$, $R^3$ and $R^4$, and reactions for their removal are described, for example, in "Protective Groups in Organic Chemistry", Plenum Press, London and New York (1973); Greene, "Protective Groups in Organic Synthesis", Wiley, N.Y. (1981); "The Peptides", Vol. I, Schröder and Lubke, Academic Press, London and N.Y. (1965); in "Methoden der organischen Chemie", Houben-Weyl, 4th Edition, Vol. 15/I, Georg Thieme Verlag, Stuttgart (1974).

Carboxylic acid protecting groups, for example, can be esters conceptually derived from lower alkanols of from 1 to 6 carbon atoms, including those branched in the 1-position and those which are substituted with one or more aromatic groups such as phenyl, or with halo or alkoxy; e.g., methyl, ethyl, t-butyl, benzyl, 4-nitrobenzyl, diphenylmethyl, methoxymethyl, and the like esters. Silyl esters such as trimethylsilyl also can be employed.

Amino protecting groups include acyl, notably alkanoyl of 2 to 6 carbon atoms, alkoxycarbonyl, each of which may be substituted with halo, alkoxy, or phenyl; e.g., acetyl, pivaloyl, 2,2,2-trichloroacetyl, benzoyl, t-butoxycarbonyl, 4-nitrobenzyloxycarbonyl, and the like.

The hydrolysis is conducted at normal temperatures utilizing dilute aqueous base, such as for example, 0.1–0.3 N aqueous alkali metal hydroxide, optionally in the presence of a water miscible organic solvent such as methanol, ethanol, tetrahydrofuran, dimethylformamide, and the like. Use of acid or strong base will lead to hydrolysis of the —N'—COR$^5$ group. Some racemization of the glutamic acid portion of the molecule may be observed.

The product of the hydrolysis initially is formed as the dicationic glutamate salt and can be readily precipitated as the free acid by adjustment of pH through acidification with, for example, acetic acid or 0.5 N hydrochloric acid. The resulting products generally are high melting crystalline or microcrystalline solids.

The intermediates of Formula II can be prepared by hydrogenating a pyrido[2,3-d]pyrimidine compound of the formula:

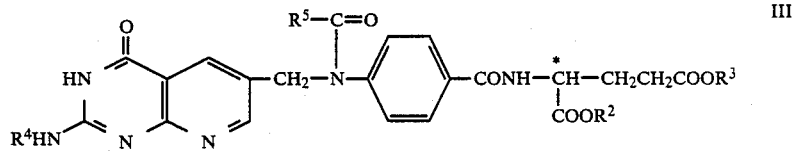

in which $R^2$, $R^3$, $R^4$, and $R^5$ are as defined above.

The hydrogenation is conducted in an acidic medium in the presence of a noble metal catalyst such as platinum, ruthenium or rhodium, including the oxides thereof and the supported forms thereof. The preferred catalyst is platinum oxide. Conditions of time, temperature, and pressure are selected so that reduction of the pyridine ring is achieved without involvement of the pyrimidine ring. A solvent such as acetic acid and a lower alkanol such as methanol or ethanol is employed.

Compounds of Formula III are prepared by acylation of a compound of the formula:

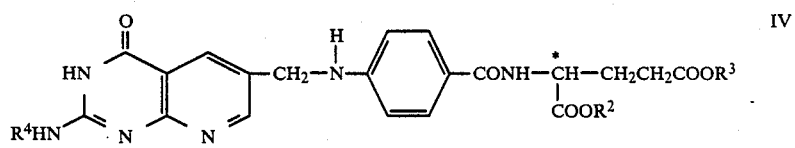

When $R^5$ is hydrogen, the acylation ("formylation") can be performed using an excess of formic acid [see e.g., Haynes et al, J. Med. Chem. 20, 588–591 (1977)]or a reactive acylating derivative of formic acid such as a mixed formic acid anhydride, as for example as is formed from formic acid and acetic anhydride.

When $R^5$ is alkyl, a reactive derivative of a carboxylic acid, as for example an acid halide such as acetyl chloride, preferably is employed.

The compounds of Formula IV can be prepared by known procedures. For example, 2-amino-4(3H)-oxo-6-formylpyrido[2,3-d]pyrimidine can be treated with an appropriate reagent to introduce the $R^4$ protecting group, such as acetic anhydride, and the resulting product allowed to react with a protected N-(4-aminobenzoyl)-L-glutamic acid derivative [see e.g., Taylor et al., J. Org. Chem., 48, 4852 (1983)].

The compounds of Formulas I and II also can be obtained by direct acylation, in the manner described above, of a compound of the formula:

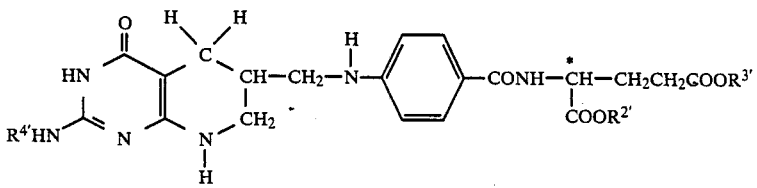

in which each of $R^{2'}$ and $R^{3'}$ is hydrogen or a carboxylic acid protecting group as defined above for $R^2$ and $R^3$, respectively, and $R^{4'}$ is hydrogen or an amino protecting group as defined above for $R^4$.

The compounds of Formulas II and III are valuable intermidiates, not only for the preparation of the final compound of Formula I but also for the preparation of the compounds of Formula V in which $R^{2'}$, $R^{3'}$, and $R^{4'}$ are all hydrogen, namely N-[4-(N'-[2-amino-4(3H)-oxo-5,6,7,8-tetrahydropyride[2,3-d]pyrimidin-6-yl-methyl[amino)benzoyl]-L-glutamic acid. This compound has antineoplastic activity and, as is known, can be prepared through direct hydrogenation of a compound of Formula IV, optionally followed by removal of any protecting groups $R^{2'}$, $R^{3'}$, and $R^{4'}$. Introduction of an N'-acyl group, such as the formyl group, prior to reduction, however, affords added protection of the amino group which, being in the nature of a benzylic amine, is susceptible to gydeogenolysis, Thus by first forming the N'-formyl derivative of Formula III, hyrdogenating the same to yield the N'-formyl-tetrahydro intermediate of Formula II, and then subjecting the same to hydrolysis, preferably acidic and basic hydrolysis performed sequentially, there is obtained N-[4-(N'-[2-amino-4(3H)-oxopyrido[2,3-d]pyrimidin-6-ylmethyl]amino)-benzoyl]-L-glutamic acid.

The compounds of Formula I can be used, alone or in combination, to treat neoplasms which in the past have been treated with methotrexate, including choriocarcinoma, leukemia, adenocarcinoma of the female breast, epidermid cancers of the head and neck, squamous or small-cell lung cancer, and various lymphosarcomas. In representative models for example, N-[4-(N'-[2-amino-4(3H)-oxo-5,6,7,8-tetrahydropyrido[2,3-d]pyrimidin-6-yl-methyl]N'-formylamino)benzoyl]-L-glutamic acid exhibited an $IC_{50}$ of 0.011 mcg/ml against CCRF-CEM cell lines (a human T-cell derived leukemia). 5-Deazafolic acid on the other hand is relatively inactive in this test. The compounds also can be used to treat certain mycosis fungoides and psoriasis.

The compounds may be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous or intraarterial. In general, the compound is administered in much the same fashion as methotrexate, but because of a different mode of action, can be administered in higher dosages than those usually employed with methotrexate. Dosage regimens must be titrated to the particular neoplasm, the condition of the patient, and the response but generally doses will be from about 10 to about 100 mg/day for 5–10 days or single daily administration of 250–500 mg, repeated periodically; e.g., every 14 days. Oral dosage forms include tablets and capsules containing from 1–10 mg of drug per unit dosage. Isotonic saline solutions containing 20–100 mg/ml can be used for parenteral administration.

The following examples will serve to further illustrate the invention.

EXAMPLE 1

Diethyl N-[4-(N'-[2-acetamido-4(3H)-oxopyrido[2,3-d]-pyrimidin-6-ylmethyl]-N'-formylamino)benzoyl]glutamate.

A mixture of 98% formic acid (25 mL) and acidic anhydride (4.9 mL, 5.25 g, 51.5 mmol) is stirred at 25° C. for 2 hours. To this solution is added 2.43 g (4.5 mmol) of diethyl N-[4-(N'-[2-acetamido-4(3H)-oxo-pyrido[2,3-d]pyrimidin-6-ylmethyl]amino)benzoyl]L-glutamate [Taylor et al. *J. Org. Chem.* 48, 4852 (1983)]. This mixture is stirred at 55° C. for 15 minutes, and at 25° C. for 1 hour. The solvent is removed under reduced pressure and the residue triturated with ether. The solid is filtered and recrystallized from 2-propanol to give 2.0 g (78%) of diethyl N-[4-(N'-[2-acetamido-4(3H)-oxopyrido[2,3-d]pyrimidin-6-ylmethyl]-N'-formylamino) benzoyl]glutamate: mp 180°–182° C.; $^1$H NMR (Me$_2$SO-d$_6$) delta 1.05–1.23 (m, 6 H), 1.95–2.10 (m, 2H), 2.16 (s, 3H), 2.49 (t, 1H, J=7.36 Hz), 3.97–4.10 (m, 4H), 4.36–4.39 (m, 1H), 5.24 (m, 2H), 7.51–7.54 (m, 2H, AA'BB'), 7.84–7.87 (m, 2H, AA'BB'), 8.21 (m, 1H), 8.69–8.75 (m, 2H), 8.82 (s, 1H).

Anal. Calcd. for $C_{27}H_{30}N_6O_8$:C, 57.24; H, 5.34; N, 14.83. Found: C, 56.94; H, 5.11; N, 14.57.

EXAMPLE 2

Diethyl N-[4-(N'-[2-pivaloylamino-4(3H)-oxopyrido[2,3-d]pyrimidin-6-ylmethyl]-N'-formylamino)benzoyl]-glutamate.

The title compound is prepared analogously to the procedure of Example 1 utilizing diethyl N-[4-(N'-[2-pivaloylamino-4(3H)-oxopyrido[2,3-d]pyrimidin-6-yl-methyl]amino)benzoyl]-L-glutamate; $^1$H NMR (Me$_2$SO-d$_6$) delta 1.09–1.16 (m, 6 H), 1.21 (s, 9H), 1.90–2.10 (m, 2H), 2.39 (t, 2H, J=7.37 Hz), 3.96–4.09 (m, 4H), 4.31–4.43 (m, 1H), 5.22 (s, 2H), 7.50–7.53 (AA'BB', 2H), 7.83–7.86 (AA'BB'), 8.21 (m, 1H), 8.71 (d, 1H, J=5.87 Hz), 8.72 (m, 1H), 8.80 (s, 1H).

EXAMPLE 3

Diethyl N-[4-(N'-[2-pivaloylamino-4(3H)-oxopyrido-[2,3-d]pyrimidin-6-ylmethyl]-N'-acetylamino)benzoyl]glutamate.

To a stirred suspension of 0.65 g of diethyl N-[4-(N'-[2-pivaloylamino-4(3H)-oxopyrido[2,3-d]-pyrimidin-6-ylmethyl]-amino)benzoyl]glutamate (1.1 mmol) and 0.22 g (2.2 mmols) of potassium bicarbonate in 10 mL of methylene chloride cooled to 0°–5° C. is added 0.097 g (1.2 mmol) of acetyl chloride. The reaction mixture is stirred at 0°–5° C. for 10 minutes and then allowed to attain room temperature. After stirring at ambient temperature for 45 minutes, 50 mL of methylene chloride are added. The mixture is extracted with 25 mL of water, 25 mL of a saturated solution of sodium bicarbonate, and again with 25 mL of water. The aqueous extracts are combined and back-extracted with 50 mL of methylene chloride. The organic extracts are dried over anhydrous magnesium sulfate, and filtered, and the solvent is removed under reduced pressure to give 0.7 g of diethyl N-[4-(N'-[2-pivaloylamino-4(3H)-oxopyrido[2,3-d]pyrimidin-6-ylmethyl]-N'-acetylamino)benzoyl]glutamate; $^1$H NMR (Me$_2$SO-d$_6$) delta 1.10–1.17 (m, 6 H), 1.22 (s, 9H), 1.88 (s, 3 H), 1.88–2.13 (m, 2H), 2.40 (t, 2H, J=7.46 Hz), 3.97–4.08 (m, 4H), 4.30–4.42 (m, 1H), 5.02 (s, 2H), 7.34–7.36 (AA'BB', 2H), 7.83–7.86 (AA'BB', 2H), 8.19 (m, 1H), 8.64 (m, 1H), 8.75 (d, 1H, J=7.39 Hz).

EXAMPLE 4

Diethyl N'-[4-(N-[2-acetamido-4(3H)-oxo-5,6,7,8-tetrahydropyrido[2,3-d]pyrimidin-6-ylmethyl]-N'-formylamino) benzoyl]-L-glutamate.

A mixture of 0.743 g (0.36 mmol) of diethyl N-[4-(N'-[2-acetamido-4(3H)-oxopyrido[2,3-d]pyrimidin-6-ylmethyl]-N'-formylamino)benzoyl]-L-glutamate and 230 mg of platinum oxide in 75 mL of a 2:1 ethanol:acetic acid solution is shaken under an atmosphere of hydrogen (40 psi) for 1.5 hours. The reaction mixture is filtered through Celite and the filtrate evaporated first under aspirator vacuum and then under high vacuum, maintaining the temperature as low as possible. The residue is dissolved in methylene chloride and chromatographed (Chromatotron) eluting with 5% methanol in methylene chloride to give 0.684 g (93%) of diethyl N-[4-(N'-[2-acetamido-4(3H)-oxo-5,6,7,8-tetrahydro pyrido[2,3-d]pyrimidin-6-ylmethyl]-N'-formylamino) benzoyl]-L-glutamate; mp 188°–190° C.; $^1$H NMR (Me$_2$SO-d$_6$) delta 1.12–1.19 (M, 6H, ester CH$_3$'s), 1.89–2.11 (m, 4H), 2.08 (s, 3H), 2.42 (t, 2H, J=7.26 Hz), 2.78–2.91 (m, 1H), 3.09–3.19 (m, 1H), 3.89 (d, 2H, J=5.98 Hz), 3.99–4.12 (m, 4H), 4.42 (m, 1H), 6.64 (m, 1H), 7.51–7.54 (m, 2H, AA'BB'), 7.91–7.94 (m, 2H, AA'BB'), 8.61 (s, 1H), 8.74 (d, 1H, J=7.32 Hz).

An analytical sample is prepared by chromatographing a portion of the above sample taking a center fraction. After removal of the solvent the sample was triturated with ether and the solid collected.

Anal Calcd. for C$_{27}$H$_{34}$N$_6$O$_8$: C, 56.83; H, 6.01; N, 14.73. Found: C, 56.60; H, 5.90; N, 14.43.

EXAMPLE 5

Diethyl N'-[4-(N-[2-pivaloylamino-4(3H)-oxo-5,6,7,8-tetrahydropyrido[2,3-d]pyrimidin-6-ylmethyl]-N'-formylamino)benzoyl]-L-glutamate.

Diethyl N'-[4-(N-[2-pivaloylamino-4(3H)-oxo-5,6,7,8-tetrahydropyrido[2,3-d]pyrimidin-6-ylmethyl]-N'-formylamino)benzoyl]-L-glutamate is similarly obtained upon reduction of diethyl N-[4-(N'-[2-pivaloylamino-4(3H)-oxopyrido[2,3-d]pyrimidin-6-ylmethyl]N'-formylamino)benzoyl]glutamate; mp 152°14 153° C.; IR (KBr) V$_{max}$ 3369 and 3250 (NH), 1732, 1637, and 1605 (C=O) cm$^{-1}$; $^1$H NMR (Me$_2$SO-d$_6$) delta 1.12–1.2 (m, 6H), 1.17 (s, 9H), 1.90–2.18 (m, 4H), 2.43 (t, 2H, J=7.4 Hz), 2.80–2.94 (m, 1H), 3.12–3.20 (m, 1 H), 3.89 (d, 2H, J=5.59 Hz), 4.00–4.11 (m, 4H), 3.90–4.47 (m, 1H), 6.40 (m, 1H), 7.52–7.55 (AA'BB', 2H), 7.92–7.94 (AA'BB', 2H), 8.62 (s, 1H), 8.75 (d, 1H, J=7.33 Hz).

Anal. Calcd. for C$_{30}$H$_{40}$N$_6$O$_6$: C, 58.81; H, 6.58; N, 13.72. Found: C, 58.53; H, 6.60; N, 13.61.

EXAMPLE 6

Diethyl N'-[4-(N-[2-pivaloylamino-4(3H)-oxo-5,6,7,8-tetrahydropyrido[2,3-d]pyrimidin-6-ylmethyl]-N'-acetylamino)benzoyl]-L-glutamate.

To a solution of 0.64 g (1.03 mmol) of diethyl N'-[4-(N-[2-pivaloylamino-4(3H)-oxopyrido[2,3-d]pyrimidin-6-ylmethyl]-N'-acetylamino)benzoyl]-L-glutamate in 40 mL of glacial acetic acid are added 96 mg of platinum oxide. The suspension is shaken under an atmosphere of hydrogen (45 psi) for 2.5 hours, mixture diluted with 100 mL of methylene chloride and filtered through Celite to remove the catalyst. The filtrate is evaporated under reduced pressure and the residue is dissolved in 100 mL of methylene chloride, and extracted twice with 75 mL portions of a saturated solution of sodium bicarbonate. The aqueous layers are back-extracted with 75 mL of methylene chloride and the organic layers are combined and dried over anhydrous magnesium sulfate. After removing the drying agent by filtration, the solvent is removed from the filtrate under reduced pressure to give 0.54 g (84% yield) of diethyl N'-[4-(N-[2-pivaloylamino-4(3H)-oxo-5,6,7,8-tetrahydropyrido[2,3-d]pyrimidin-6-ylmethyl]-N'-acetylamino)benzoyl]glutamate which can be further purified by recrystallization from ethyl acetate; mp 120°–123° C. $^1$H NMR (Me$_2$SO-d$_6$) delta 1.06–1.19 (m, 6 H), 1.16 (s, 9H), 1.82 (s, 3H) 1.84–2.17 (m, 6H), 2.42 (t, 2H, J=7.40 Hz), 2.80–2.94 (m, 1H), 3.17–3.23 (m, 1 H), 3.68 (d, 2H, J=5.59 Hz), 3.98–4.10 (m, 4H), 4.39–4.45 (m, 1H), 6.38 (s, 1H), 7.43–7.46 (AA'BB', 2H), 7.90–7.93 (AA'BB', 2H), 8.79 (d, 1H, J=7.33 Hz).

EXAMPLE 7

N-[4-(N'-[2-amino-4(3H)-oxo-5,6,7,8-tetrahydropyrido[2,3-d]pyrimidin-6-ylmethyl]-N'-formylamino)benzoyl]L-glutamic acid.

A mixture of 0.092 g (0.16 mmol) of diethyl N-[4-(N'-[2-acetamido-4(3H)-oxo-5,6,7,8-tetrahydropyrido[2,3-d]pyrimidin-6-ylmethyl]-N'-formylamino)benzoyl]-L-glutamate in 10 mL of a 0.25 aqueous sodium hydroxide solution is stirred at 25° C. for 72 hours and then water evaporated under reduced pressure. The residue is dissolved in 15 mL of water, and the solution is cooled to 0° C. and acidified with acetic acid. The solid is collected after 30 minutes to give 0.046 g (60.5%) of N-[4-(N'-[2-amino-4(3H)-oxo-5,6,7,8-tetrahydropyrido 2,3-d]pyrimidin-6-ylmethyl]-N'-formylamino)benzoyl]-L-glutamic acid, $^1$H NMR (Me$_2$SO-d$_6$) delta 1.81–2.2 (m,4H), , 2.33 (m, 3H), 2.73 (m, 1H), 3.1 (m, 1H), 3.85 (m, 2H), 4.39 (m, 1H), 6.2 (m, 1H), 7.49–7.51 (m, 2H, AA′BB′), 7.90–7.93 (m, 2H, AA′BB′), 8.59–8.62 (m, 2H).

Analogously, 200 mg of diethyl N'-[4-(N-[2-pivaloylamino-4(3H)-oxo-5,6,7,8-tetrahydropyrido[2,3-d]pyrimid-6ylmethyl -N'-acetylamino)benzoyl]-L-glutamate is stirred for 72 hours in 5 mL of 0.2 N sodium hydroxide. The reaction mixture is neutralized with 0.5 hydrochloric acid, cooled to 0° C., and the solid which forms is collected by filtration to yield N-[4-(N'-[2-ami (3H)-oxo-5,6,7,8-tetrahydropyrido[2,3-d]-pyrimid ]-N'-acetylamino)benzoyl]-L-glutamic acid.

EXAMPLE 8

N-[4-(N'-(3H)-oxo-5,6,7,8-tetrahydropyrido[2 imidin-6-ylmethyl]-N'-formylamino)benzoyl]-L-glutamic acid.

A solution of 20 mg of N-[4-(N'-[2-amino-4(3H)-6,7,8-tetrahydropyrido[2,3-d]pyrimidin-6-yl -amino)-benzoyl]-L-glutamic acid in 0.5 mL of 97% formic acid is heated at 90° C. for 1 hour. The solvent is removed under reduced pressure and the residue triturated with ether. The insoluble solid is collected give 17 mg of product, N-[4-(N'-[2-amino-4(3H)-o 6,7,8-tetrahydropyrido[2,3-d]pyrimidin-6-y'-formylamino)benzoyl]-L-glutamic acid, which is further purified by dissolution in 0.1 N sodium hydroxide and precipitation through the addition of glacial acetic acid.

EXAMPLE 9

N-[4-(N'-[2-amino-4(3H)-oxo-5,6,7,8-tetrahydropyrido[2,3-d]pyrimidin-6-ylmethyl]amino)benzoyl]-L-glutamic acid.

To 32 mL of a 5% of hydrochloric acid in methanol solution (prepared by diluting 2 mL of concentrated hydrochloric acid to 60 mL with methanol) is added 0.717 g (1.3 mmol) of diethyl N-[4-(N'-[2-acetamido--4(3H)-oxo-5,6,7,8-tetrahydropyrido[2,3-d]pyrimidin-6-ylmethyl]-N'-formylamino)benzoyl]-L-glutamate (prepared as in Example 2). The reaction mixture is stirred at 45° C. for 18 hours. After allowing the reaction mixture to cool at 25° C., 4 mL of sodium hydroxide (6 N) are added and the mixture stirred for another 72 hours at 25° C. The solution is concentrated under reduced pressure. Twenty milliliters of water are added, and the mixture acidified by adding glacial acetic acid dropwise. After standing 2 hours at 0° C., the solid is collected to give 0.485 g (88% yield) of N-[4-(N'-[2-amino-4(3H)-oxo-5,6,7,8-tetrahydropyrido[2,3-d]pyrimidin-6-ylmethyl]amino)benzoyl]-L-glutamic acid; mp decomposition beginning at 198° C.; $^1$H NMR (Me$_2$SO-d$_6$) delta 1.86–2.1 (m, 6H), 2.31 (t, 2H, J=7.2), 2.8–2.86 (m, 1H), 3.24–3.28 (m, 2H), 4.2–4.4 (m, 1H), 25 5.94 (s, 2H), 6.29 (s, 1H), 6.34 (t, 1H, J=5.24), 6.56–6.58 (AA′BB′, 2H), 7.62–7.65 (AA′BB′, 2H), 8.06 (d, J=5.15), 9.7 (br, s, 1H).

The same product can be obtained through hydrolysis of diethyl N-[4-(N'-[2-pivaloylamino-4(3H)-oxopyrido[2,3-d]pyrimidin-6-ylmethyl]-N'-formylamino)benzoyl]glutamate.

Alternatively, 1.44 g (2.4 mmols) of diethyl N'-[4-(N-[2-pivaloylamino-4(3H)-oxo-5,6,7,8-tetrahydropyrido[2,3-d]pyrimidin-6-ylmethyl]-N'-formylamino)benzoyl]-L-glutamate is dissolved in 1N sodium hydroxide and the solution is stirred at 25° C. for 72 hours. Charcoal is added and the suspension is stirred and filtered. The filtrate is acidified with glacial acetic acid and the white solid is collected after 30 minutes cooling at 0° C. to yield 0.87 g (84% yield) of the same product; mp slow decomposition over 198° C.; IR (KBr) V$_{max}$ 3460–2500 (NH and COOH), 1695, 1655, and 1600 (C=O) cm$^{-1}$; $^1$H NMR (Me$_2$SO-d$_6$) delta 1.85–2.02 (m, 6 H), 2.3 (t, 2H, J=7.4 Hz), 2.81–2.88 (m, 1H) 3.23–3.32 (m, 2H) 4.2–4.4 (m, 1H), 5.92 (s, 2H), 6.34 (t, 1H, J=5.28 Hz), 6.55–6.57 (m, 2H AA′BB′), 7.61–7.64 (AA′BB′, 2H), 8.08 (d, 1H, J=7.64 Hz), 9.7 (br, s, 1H).

What is claimed is:

1. A compound selected from the group consisting of:
(i) 4(3H)-oxo-5,6,7,8-tetrahydropyrido[2,3-d]pyrimidines of the formula:

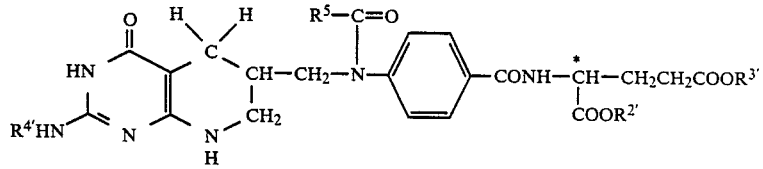

wherein
R$^{2'}$ and R$^{3'}$ are hydrogen or the same or different carboxylic acid protecting group selected from the group consisting of straight or branched chain alkyl of 1 to 6 carbon atoms, unsubstituted or substituted with one or more phenyl, halo, or alkoxy groups, and silyl;
R$^{4'}$ is hydrogen or an amino protecting group selected from the group consisting of alkanoyl and alkoxycarbonyl of 2 to 6 carbon atoms, each of which is unsubstituted or substituted with halo, alkoxy or phenyl;
R$^5$ is hydrogen or alkyl of 1 to 6 carbon atoms; and the configuration about the carbon atom designated * is L; and
(ii) the tautomeric forms thereof at least one of R$^{2'}$, R$^{3'}$ and R$^{4'}$ being other than hydrogen.

2. A compound according to claim 1 wherein R$^5$ is hydrogen, each of R$^{2'}$ and R$^{3'}$ is alkyl of 1 to 6 carbon atoms and R$^{4'}$ is alkanoyl of 2 to 6 carbon atoms.

3. The compound according to claim 2 in which each of R$^{2'}$ and R$^{3'}$ is ethyl, and R$^{4'}$ is acetyl.

4. The compound according to claim 2 in which each of R$^{2'}$ and R$^{3'}$ is ethyl, and R$^{4'}$ is pivaloyl.

5. A compound according to claim 1 wherein R$^5$ is methyl, each of R$^{2'}$ and R$^{3'}$ is alkyl of 1 to 6 carbon atoms and R$^{4'}$ is alkanoyl of 2 to 6 carbon atoms.

6. The compound according to claim 5 in which each of R$^{2'}$ and R$^{3'}$ is ethyl, and R$^{4'}$ is acetyl.

7. The compound according to claim 5 in which each of R$^{2'}$ and R$^{3'}$ is ehtyl, and R$^{4'}$ is pivaloyl.

8. A compound of the formula:

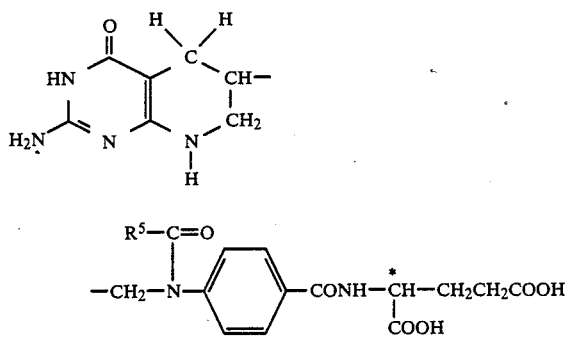

wherein:

R$^5$ is hydrogen or alkyl of 1 to 6 carbon atoms;

the configuration about the carbon atom designated * is L, and the tautomeric forms thereof and the pharmaceutically acceptable alkali metal, alkaline earth metal, ammonium, and substituted amonium salts thereof.

9. A compound according to claim 8 selected from the group consisting (i) of N-[4-(N'-[2amino-4(3H)-oxo-5,6,7,8-tetrahydropyrido[2,3-d]pyrimidin-6-yl-methyl]-N'-formylamino)benzoyl]-L-glutamic acid, (ii) N-[4-(N'-[2-amino-4(3H)-oxo-5,6,7,8-tetrahydropyrido[2,3-d]pyrimidin-6-ylmethyl]-N'-acetylamino)benzoyl]-L-glutamic acid, and (iii) the pharmaceutically acceptable alkali metal, alkaline earth, non-toxic metal, ammonium, and substituted ammonium salts thereof.

10. The compound according to claim 9 which is N-[4-(N'-[2-amino-4(3H)-oxo-5,6,7,8-tetrahydropyrido[2,3-d]pyrimidin-6-ylmethyl]-N'-formylamino)benzoyl]-L-glutamic acid.

11. The compound according to claim 9 which is N-[4-(N'-[2-amino-4(3H)-oxo-5,6,7,8-tetrahydropyrido[2,3-d]pyrimidin-6-ylmethyl]-N'-acetylamino)benzoyl]-L-glutamic acid.

12. The method of combating neoplastic growth in a mammal which comprises administering to the mammal in a single or multiple dose regimen an effective amount of a compound according to claim 10.

13. A pharmaceutical composition for combating neoplastic growth in a mammal which comprises an amount of a compound according to claim 10 which upon administration to the mammal in a single or multiple dose regimen is effective to combat said growth, in combination with a pharmaceutically acceptable carrier.

14. The method of combating neoplastic growth in a mammal which comprises administering to the mammal in a single or multiple dose regimen an effective amount of a compound according to claim 11.

15. A pharmaceutical composition for combating neoplastic growth in a mammal which comprises an amount of a compound according to claim 11 which upon administration to the mammal in a single or multiple dose regimen is effective to combat said growth, in combination with a pharmaceutically acceptable carrier.

* * * * *